United States Patent [19]

Monteil et al.

[11] Patent Number: 4,645,778
[45] Date of Patent: Feb. 24, 1987

[54] 2-(N-PYRROLIDINO)-3-ISOBUTOXY-N-SUBSTITUTED-PHENYL-N-BENZYL-PROPYLAMINES, THEIR PREPARATION AND PHARMACEUTICAL USE

[75] Inventors: André J. Monteil, Chatel-Guyon; Jacques A. Simond, Les-Martres-De-Veyre; Michel Combourieu, Aurillac, all of France

[73] Assignee: Riom Laboratoires C.E.R.M. "RL-Cerm"S.A., Riom, France

[21] Appl. No.: 654,921

[22] Filed: Sep. 27, 1984

[30] Foreign Application Priority Data

Sep. 27, 1983 [FR] France ................. 8315367

[51] Int. Cl.$^4$ .................. C07D 207/06; A61K 31/40
[52] U.S. Cl. .................. 514/422; 514/428; 548/526; 548/569
[58] Field of Search ........... 548/526, 569; 514/428, 514/422

[56] References Cited

U.S. PATENT DOCUMENTS

Re. 30,577  4/1981  Busch et al. ............ 544/124 X
3,962,238  1/1976  Mauvernay et al. ....... 544/124 X

FOREIGN PATENT DOCUMENTS 2504925  5/1982  France .
2087233  5/1982  United Kingdom .

Primary Examiner—Donald G. Daus
Assistant Examiner—William A. Teoli, Jr.
Attorney, Agent, or Firm—Wegner & Bretschneider

[57] ABSTRACT

Compounds of the formula:

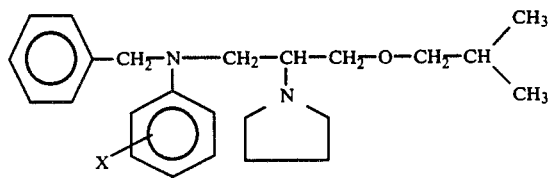

in which X represents one or two radicals selected from halogen, hydroxyl, alkoxy, alkyl, trifluoromethyl or methylenedioxy radicals, and their pharmaceutically acceptable salts, which may be used in the treatment of cardiovascular disturbances such as angina pectoris, hypertension and rhythmic disorders.

10 Claims, No Drawings

2-(N-PYRROLIDINO)-3-ISOBUTOXY-N-SUBSTITUTED-PHENYL-N-BENZYL-PROPYLAMINES, THEIR PREPARATION AND PHARMACEUTICAL USE

The present invention relates to novel 2-(N-pyrrolidino)-3-isobutoxy-N-substituted-phenyl-N-benzyl-propylamines, their preparation and their pharmaceutical use.

More precisely, these novel derivatives correspond to the following general formula:

[structure (I)]

in which X represents one or two radicals selected from halogen, hydroxyl, alkoxy, alkyl, trifluoromethyl or methylenedioxy radicals.

The invention also relates to the addition salts of the compounds of formula I with inorganic or organic pharmaceutically acceptable acids, such as hydrochloric acid, fumaric acid, maleic acid, citric acid or succinic acid, these acids being mentioned by way of illustration but without implying any limitation.

Amongst the compounds of formula I and their salts the most preferred compounds are those in which X represents a di-substitution pattern, whereby both substituents are preferably the same, such as a di-halo, di-methyl, di-methoxy or methylenedioxy substitution pattern. Most preferred in this connection are the ortho, ortho dimethyl, the meta, para dihalo and the meta, para methylenedioxy substitution patterns.

Another preferred embodiment of the present invention—if X is a mono substituent—is represented by those compounds of formula I, in which X is a substituent in meta- or para-position. Most preferred are the compounds I in which X represents a meta-chloro, para-chloro, meta-methoxy or para-methoxy group.

Pharmacological studies have shown the compounds of the invention to possess valuable cardiovascular properties and particularly anti-anginal, anti-hypertensive and anti-dysrythmic properties; this cardiovascular profile being surprisingly more potent and more specific than that of the prior art compounds.

The compounds of the invention can be prepared in various manners well known in the preparation of analogous compounds.

A convenient process for the preparation of the present compounds consists of a condensation reaction of a compound of the formula:

[structure A]

or an acid addition salt thereof, in which Hal means halogen, preferably chlorine with a compound of the formula:

[structure B]

or an acid addition salt thereof, in which X has the aforesaid meaning and Q represents either oxygen or two hydrogen atoms (2H), after which—if Q is oxygen—the resulting carbonyl containing compound is reduced with a hydrogenating agent.

In the aforesaid condensation reaction the compound [B] is preferably reacted with the compound of formula [A] in the presence of a basic substance such as sodium-hydroxide or a quaternary ammonium compound.

According to a variant of this condensation reaction the compound of formula B is first metallised with the aid of agents well known to those skilled in the art, such as sodiumhydride or sodium, potassium or lithiumamide, in an organic solvent such as benzene, toluene, xylene, dimethylformamide or dimethylsulfoxide.

The optional hydrogenation (if Q=O) is carried out preferably with a metalhydride or complex metalhydride, such as for example with diborane.

The starting compound of formula [B] may be prepared by reaction of

[structures C and D]

if desired, followed by hydrogenation of the resulting compound.

The cardiovascular properties of the compounds of the invention were demonstrated by pharmacological experiments carried in vitro and in vivo. In vitro, the calcium antagonism activity was investigated in accordance with the methods summarised below.

Investigation of a cardiac tropism

A rabbit's papillary muscle was placed in a KREBS-HENSELEIT solution kept at 37° C. and was stimulated electrically at a frequency of 1.5 Hz (5 ms of pulse at 15 V).

The positive inotropic effect of calcium chloride was investigated by the method of cumulative dose-response curves.

The substances to be studied were added to the solution in which the muscle was kept, 15 minutes prior to determining the agonist curves.

Investigation of a vascular tropism

A rabbit's isolated aorta, cut into spirals, was placed in a KREBS solution kept at 37° C., free from $Ca^{++}$ and enriched with $K^+$ (6 mg of KCL/liter) for depolarisation.

The contracting effect of cumulative concentrations of calcium chloride was investigated and the anti-calcium effect of the compounds studied was evaluated 15 minutes after their addition to the solution in which the aorta was kept.

The conventional parameters of molecular pharmacology are subsequently determined ($pA_2$ for a competitive antagonism and $pD'_2$ for a non-competitive anatagonism), using the technique of VAN ROSSUM [ARCH. INT. PHARMACODYN. THER. 143, 299–330 (1963)].

These results are shown in the following table.

TABLE I

| Comp. No. see Table III | PAPILLARY MUSCLE | | ISOLATED AORTA | |
|---|---|---|---|---|
| | pA$_2$ | pD'$_2$ | pA$_2$ | pD'$_2$ |
| 1 | 4.30 ± 0.24 | 3.81 ± 0.20 | 4.83 ± 0.28 | 5.08 ± 0.27 |
| 3 | 4.87 ± 0.40 | 4.5 at 10$^{-4}$ M | 4.70 ± 0.38 | 4.00 ± 0.24 |
| 5 | Inactive at 10$^{-4}$ M | / | 4.83 ± 0.27 | 4.71 ± 0.20 |
| 6 | 3.41 at 10$^{-4}$ M | / | 5.19 ± 0.37 | 3.73 ± 0.50 |
| 7 | Inactive at 10$^{-4}$ M | / | 4.70 ± 0.60 | 3.85 ± 0.43 |
| 8 | 4.67 at 10$^{-5}$ M | 3.69 at 10$^{-4}$ M | 5.21 ± 0.65 | 4.87 ± 0.48 |
| 11 | 5.44 ± 0.26 | total inhibition at 10$^{-4}$ M | 4.94 ± 0.43 | 4.80 ± 0.05 |

These results show that the compounds of the invention possess valuable anti-calcium properties, compound No. 11 being the compound with about the highest activity both in the cardiac test and the vascular test; the activity of compound No. 8 is also noteworthy. On the other hand, it is found that compounds 1 and 3 exhibit a more marked cardiac tropism whilst compound No. 6 exhibits a predominantly vascular tropism.

In vivo, the anti-angina activity was investigated by measuring the haemodynamic effects in the anaesthetised dog, in accordance with the method summarised below.

The following parameters were recorded on the dog anaesthetised with chloralose (100 mg.kg$^{-1}$ administered intravenously):

pulse rate, by means of subcutaneous ECG electrodes connected to a BECKMAN cardiotachymeter (branch D II), coronary arterial flow recorded by means of a STATHAM electromagnetic flowmeter and antitachycardiac action (inhibition of the positive chronotropic effects of isoprenaline).

These parameters were recorded continuously on a BECKMAN dynograph and at the same time the duration of the action was measured.

The compounds of the invention are administered intravenously at a dose of 5 mg.kg$^{-1}$.

The results recorded, expressed in the form of percentage variations, are summarised in Table II below.

TABLE II

| Comp. No. see Table III | PULSE RATE | | CORONARY FLOW | | ANTI-TACHYCARDIAC ACTION | |
|---|---|---|---|---|---|---|
| | Variation (%) | Duration (min) | Variation (%) | Duration (min) | Variation (%) | Duration (min) |
| 2 | −11 | >45 | +39 | 10 | −51 | 15 |
| 3 | −24 | >45 | +196 | 20 | −63 | 30 |
| 4 | −27 | >45 | +32 | 3 | −60 | >45 |
| 5 | −20 | >45 | +98 | 15 | −45 | 15 |
| 6 | −32 | >45 | +20 | 1 | −64 | >45 |
| 7 | −23 | 45 | +31 | 5 | −54 | 45 |
| 8 | −36 | 35 | +85 | 15 | −28 | 15 |
| 11 | −50 | >45 | +116 | 20 | −47 | 45 |

These results show that the compounds of the invention all show bradycardic activity after intravenous administration at a dose of 5 mg.kg$^{-1}$. Moreover, the majority of these substances possess a powerful anti-tachycardiac action. It appears that the compounds possessing the most valuable anti-anginal activity are compounds 11, 8, 2, 3 and 5.

The compounds of the invention have moreover been found to have a low toxicity. Their acute toxicity on oral administration to mice generally corresponds to a dose greater than 500 mg-kg$^{-1}$.

This set of pharmacological properties shows the possibility of applying the compounds of the invention in human therapy, as drugs for the treatment of cardiovascular disorders, such as angina pectoris, hypertension or rhythmic disturbances.

When combined with conventional pharmaceutical excipients, the compounds can be administered enterally or parenterally, preferably orally or intravenously at daily doses of between 1 and 15 mg per kg of body weight.

Mixed with suitable auxiliaries the compounds I or a salt thereof may be compressed into solid dosage units such as pills, tablets etc., or may be processed into capsules. By means of suitable liquids the compounds may also be applied as an injection- or oral-preparation in the form of solutions, suspensions or emulsions.

The compounds of formula I possess a chiral carbon, as a result of which a racemic mixture I and separate optical enantiomers I are possible. Both the racemic mixture, as well as the separate optical enantiomers belong to the compounds according to the invention. The separate optical enantiomers can be prepared in the usual manner by resolution of the racemic mixture or directly using optically active starting products.

The alkyl group in the definition of X is a linear or branched alkyl group with 1 to 6 carbon atoms, and more particularly with 1 to 4 carbon atoms, such as methyl, ethyl, propyl, butyl or isobutyl. The methyl group is most preferred.

The alkyl radical in the alkoxy group defined in X has a similar meaning.

Halogen in the definition of X is preferably chlorine or bromine.

EXAMPLE 1

2-(N-pyrrolidino)-3-isobutoxy-N-(3,4-methylenedioxy)-phenyl-N-benzyl-propylamine.

42 g (0.3 M) of benzoyl chloride were introduced dropwise, at ambient temperature, into a reactor containing 41 g (0.3 M) of 3,4-methylenedioxy aniline and 75 ml (0.9 M) of triethylamine in 500 ml of toluene, and the mixture was then heated for 4 hours at 40° C. The reaction mixture having been allowed to return to ambient temperature, a further 20 g of benzoyl chloride and 30 ml of triethylamine were added and the mixture was heated at 40° C. for 9 hours. At the end of the reaction, the precipitate formed was filtered off and washed with a sodium carbonate solution and then with water.

The product was then taken up in methylene chloride, the solution washed with water, the organic phase dried and the solvent distilled off. This gave 40 g of 3',4'-methylenedioxy-benzanilide of melting point 136° C.

In a second stage, 15 g (0.06 M) of the above amide were introduced into a reactor containing 100 ml of 10 N sodium hydroxide solution and this mixture was heated for 3 hours at 80° C. and allowed to return to ambient temperature, after which 1.3 g (0.006 M) of benzyltriethylammonium chloride and 15 g of 1-(2- chloro-3-isobutoxy)-propylpyrrolidine were added and the mixture was heated for 6 hours at 70° C. The amide formed was extracted with methylene chloride; the organic phase was dried, the solvent removed and the residue distilled, giving 18 g of N-[2-(N-pyrrolidino)-3-isobutoxy]-propyl-3',4'-methylenedioxy-benzanilide, of boiling point 213° C./0.5 mm Hg.

In the third stage, 6 g (0.12 M) of sodium borohydride were introduced into 75 ml of tetrahydrofuran, and 17 g (0.039 M) of the above amide, dissolved in 35 ml of tetrahydrofuran, were then added dropwise. Whilst the reaction mixture was kept under a stream of nitrogen, 37 ml of boron trifluoride ethyl etherate dissolved in 50 ml of tetrahydrofuran were then added dropwise, after which the reaction was allowed to proceed for 4 hours, with stirring. The mixture was then hydrolysed by adding 60 ml of a 2 N hydrochloric acid solution, and the solvent thereafter removed by distillation. The mixture was rendered alkaline with 2 N NaOH, the base was extracted with methylene chloride, the organic phase was dried and the solvent removed. After conversion of the product thus obtained to the fumarate and recrystallisation of the latter from ethanol, 13.5 g of the product shown in the title were obtained in the form of the fumarate, having a melting point of 124° C. and the following elementary analysis:

|  | C % | H % | N % |
|---|---|---|---|
| Calculated | 66.14 | 7.27 | 5.32 |
| Found | 66.15 | 7.16 | 5.26 |

EXAMPLE 2

2-(N-pyrrolidino)-3-isobutoxy-N-(3-chloro)-phenyl-N-benzyl-propylamine

Following the procedure of the preceding example, 3'-chloro-benzanilide was first prepared and this was then treated, as described in Example 1 with 1-(2-chloro-3-isobutoxy)-propylpyrrolidine to give N-2-(N-pyrrolidino)-3-isobutoxy]-propyl-3'-chloro-benzanilide.

This amide was subsequently reduced. A solution of 24 ml of BF$_3$Et$_2$O in 15 ml of THF was introduced dropwise into a reactor containing a suspension of 5.1 g of sodium borohydride in 30 ml of THF kept at between 0° and 5° C. The reaction was then allowed to take place at ambient temperature under a stream of nitrogen, whilst stirring was continued for 4 hours. The reaction mixture was then hydrolysed by adding 100 ml of (20%) hydrochloric acid followed by 100 ml of water. After the organic solvent had been removed by distillation, the residue was rendered alkaline with 10 N sodium hydroxide solution and the compound shown in the title was then extracted with methylene chloride.

After the extract had been dried and the solvent removed, the compound was converted to the fumarate in a mixture of ethanol and ether and was recrystallised from ethyl acetate. This gave 10 g of product having a melting point of 109° C. and the following elementary analysis:

|  | C % | H % | N % |
|---|---|---|---|
| Calculated | 65.04 | 7.21 | 5.42 |
| Found | 66.20 | 7.32 | 5.49 |

EXAMPLE 3

2-(N-pyrrolidino)-3-isobutoxy-N-(4-hydroxy)phenyl-N-benzyl-propylamine

Starting from 4-benzyloxy aniline and benzoyl chloride, 4'-benzyloxy-benzanilide was first obtained and this was reacted with 1-(2-chloro-3-isobutoxy)-propylpyrrolidine to give N-[2-(N-pyrrolidino)-3-isobutoxy]-propyl-4'-benzyloxy-benzanilide.

This compound was subsequently debenzylated by catalytic hydrogenation. 3.7 g Of catalyst (5% Pd/C) and 37 g of the above amide were introduced into a Parr apparatus containing 370 ml of absolute ethanol, the reaction mixture was then brought to pH 1 by adding ethanol saturated with HCl, and the mixture was then stirred under a hydrogen pressure of 28 kg/cm$^2$ for 4 days, the catalyst being changed twice. When the reaction had ended, the catalyst was filtered off and the ethanol was removed by distillation. The residue was rendered alkaline with ammonia, and the base was extracted with methylene chloride, giving 27 g of N-[2-(N-pyrrolidino)-3-isobutoxy]-propyl-4'-hydroxy-benzanilide.

In a last stage, the amide obtained was reduced as indicated in the preceding examples.

On reacting 26 g of amide, 11 g of NaBH$_4$ and 50 ml of BF$_3$Et$_2$O in THF for 6 hours at the reflux temperature of the solvent and then hydrolysing the mixture in the cold by means of 180 ml of 6 N hydrochloric acid, 15.8 g of the compound shown in the title were obtained in the form of the dihydrochloride having a melting point of 131° C. and the following elementary analysis:

|  | C % | H % | N % |
|---|---|---|---|
| Calculated | 63.29 | 7.96 | 6.15 |
| Found | 63.10 | 8.06 | 6.02 |

The compounds of the preceding examples together with some additional compounds of the invention (all prepared according to example 1) are summarised in the following table.

TABLE III

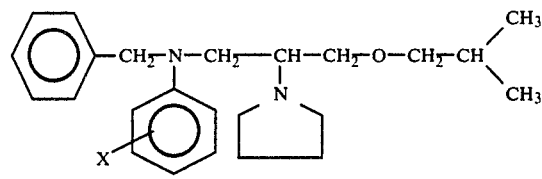

| No. Compound | X | Salt | m.p. °C. |
|---|---|---|---|
| 1 | 4-CH$_3$ | fumarate | 127 |
| 2 | 3,4-diCl | — | 68 |
| 3 | 4-OCH$_3$ | fumarate | 136 |
| 4 | 4-Cl | — | 74 |
| 5** | 3-Cl | fumarate | 109 |
| 6 | 3-CF$_3$ | HCl | 150 |
| 7 | 3,5-diCl | HCl | 142 |
| 8 | 2,6-di-CH$_3$ | HCl | 181 |
| 9 | 2-OCH$_3$ | fumarate | 104 |
| 10*** | 4-OH | 2.HCl | 131 |
| 11* | 3,4 O—CH$_2$—O | fumarate | 124 |
| 12 | 3-Br | oxalate | 137.5 |

*the compound of Example 1
**the compound of Example 2
***the compound of Example 3.

We claim:
1. A compound of the formula:

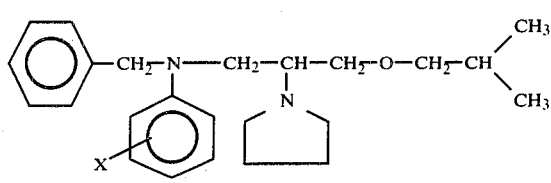

wherein X represents halogen, hydroxy, alkoxy, alkyl or trifluoromethyl or wherein $X_2$ represents methylenedioxy, and pharmaceutically acceptable salts thereof.

2. A compound of claim 1, wherein $X_2$ represents dihalo, dimethyl, dimethoxy or methylenedioxy.

3. A compound of claim 2 which is 2-(N-pyrrolidino)-3-isobutoxy-N-(3,4-methylenedioxyphenyl)-N-benzyl-propylamine.

4. A compound of claim 2 which is 2-(N-pyrrolidino)-3-isobutoxy-N(2,6-dimethylphenyl)-N-benzyl-propylamine.

5. A compound of claim 2 which is 2-(N-pyrrolidino)-3-isobutoxy-N-(3,4-dichlorophenyl)-N-benzyl propylamine.

6. Pharmaceutical composition useful as a drug for cardiovascular disorders, especially angina pectoris, hypertension and rhythmic disorders, characterized in that it contains, as the active principle, an effective amount of at least one of the compounds of claim 1, together with appropriate excipients.

7. Pharmaceutical composition useful as a drug for cardiovascular disorders, especially angina pectoris, hypertension and rhythmic disorders, characterized in that it contains, as the active principle, an effective amount of at least one of the compounds of claim 2, together with appropriate excipients.

8. Pharmaceutical composition useful as a drug for cardiovascular disorders, especially angina pectoris, hypertension and rhythmic disorders, characterized in that it contains, as the active principle, an effective amount of the compound of claim 3, together with appropriate excipients.

9. Pharmaceutical composition useful as a drug for cardiovascular disorders, especially angina pectoris, hypertension and rhythmic disorders, characterized in that it contains, as the active principle, an effective amount of the compound of claim 4, together with appropriate excipients.

10. Pharmaceutical composition useful as a drug for cardiovascular disorders, especially angina pectoris, hypertension and rhythmic disorders, characterized in that it contains, as the active principle, an effective amount of the compound of claim 6, together with appropriate excipients.

* * * * *

UNITED STATES PATENT AND TRADEMARK OFFICE
CERTIFICATE OF CORRECTION

PATENT NO. : 4,645,778
DATED : February 24, 1987
INVENTOR(S) : Andre Jean-Claude Monteil et al It is certified that error appears in the above-identified patent and that said Letters Patent is hereby corrected as shown below:

Column 8, Claim 10, line 26, "Claim 6" should read -- Claim 5 --.

Signed and Sealed this

Twenty-sixth Day of April, 1988

*Attest:*

DONALD J. QUIGG

*Attesting Officer*    *Commissioner of Patents and Trademarks*